US006239326B1

(12) United States Patent
Howe (10) Patent No.: US 6,239,326 B1
(45) Date of Patent: May 29, 2001

(54) SPARC-DEFICIENT TRANSGENIC MICE

(75) Inventor: Chin C. Howe, Wilmington, DE (US)

(73) Assignee: The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 09/297,751

(22) PCT Filed: Nov. 6, 1997

(86) PCT No.: PCT/US97/20320

§ 371 Date: May 5, 1999

§ 102(e) Date: May 5, 1999

(87) PCT Pub. No.: WO98/20112

PCT Pub. Date: May 14, 1998

Related U.S. Application Data (60) Provisional application No. 60/030,572, filed on Nov. 7, 1996.

(51) Int. Cl.[7] .................. A01K 67/027; G01N 33/00; C12N 5/00; C12N 15/00
(52) U.S. Cl. ........................ 800/18; 800/3; 800/8; 800/9; 800/25; 435/354; 435/455; 435/29
(58) Field of Search .................. 800/3, 14, 25, 800/18, 8, 9; 435/29, 351, 455

(56) References Cited

FOREIGN PATENT DOCUMENTS

WO 98/20112   5/1998 (WO).

OTHER PUBLICATIONS

J. Schwarzbauer and C. Spencer, "The *Caenorhabditis elegans* Homologue of the Extracellular Calcium Binding Protein SPARC/Osteonectin Affects Nematode Body Morphology and Mobility," *Mol. Biol. Chem.*, 4:941–952 (Sep. 1993).
L. Purcell et al., "Developmental Anomalies of Xenopus Embryos Following Microinjection of SPARC Antibodies," *J. Exp. Zool.*, 265:13–164 (Feb. 1, 1993).
M. Evans et al., "Establishment in Culture of Pluripotential Cells fro Mouse Embryos," *Nature*, 292:154–156 (Jul. 1981).
A. Poustka et al., "Selective Isolation of Cosmid Clones by Homologous Recombination in *Escherichia coli*," *Proc. Natl. Acad. Sci. USA*, 81:4129–4133 (Jul. 1984).
C. C. Howe et al., "Expression of SPARC/osteonectin Transcript in Murine Embryos and Gonads," *Differentiation*, 37:20–25 (1988).

J.H. McVey et al., "Characterization of the Mouse SPARC/Osteonectin Gene," *J. Biol. Chem.*, 263(23)11111–11116 (Aug. 15, 1988).
S. Thompson et al., "Germ Line Transmission and Expression of a Corrected HPRT Gene Produced by Gene Targeting in Embryonic Stem Cells," *Cell*, 56:313–321 (Jan. 27, 1989).
Bradley et al (1992) Bio/Technology 10, 534–539.*
Mullins et al (1996) J. Clin. Invest. 98. S37–S40.*
Seamark et al (1994) Reprod. Fertil. Dev. 6, 653–657.*
Moreadith et al (1997) J. Mol. Med. 75, 208–216.*
Capecchi (Mar. 1994) Scientific American, 34–41.*
T. Lane and E. Sage, "The Biology of SPARC, a Protein That Modulates Cell–Matrix Interactions," *FASEB J.*, 8:163–173 (Feb. 1994).
M. Ledda et al. "Suppression of SPARC Expression by Antisense RNA Abrogates the Tumorigenicity of Human Melanoma Cells," *Nature Med.*, 3(2):171–176 (Feb. 1997).
S. Mok et al., "SPARC, an Extracellular Matrix Protein with Tumor–Suppressing Activity in Human Ovarian Epithelial Cells," *Oncogene*, 12:1895–1901 (May 2, 1996).
S. Funk and E. Sage, "Differential Effects of SPARC and Cationic SPARC Peptides on DNA Synthesis by Endothelial Cells and Fibroblasts," *J. Cell. Physiol.*, 154:53–63 (Jan. 1993).
E. Sage and P. Bornstein, "Extracellular Proteins that Modulate Cell–Matri Interactions," *J. Biol. Chem.*, 266(23):14831–14834 (Aug. 15, 1991).
M. Reed et al., "Differential Expression of SPARC and Thrombospondin 1 in Wound Repair: Immunolocalization and In Situ Hybridization ," *J. Histochem. Cytochem.*, 41(10):1467–1477 (Oct. 1993).
I. Mason et al., "Evidence from Molecular Cloning that SPARC, a Major Product of Mouse Embryo Parietal Endoderm, is Related to an Endothelial Cell 'Culture Shock' Glycoprotein of $M_r$ 43 000," *EMBO J.*, 5(7):1465–1472 (Jul. 1986).

* cited by examiner

*Primary Examiner*—Deborah Crouch
(74) *Attorney, Agent, or Firm*—Howson and Howson (57) ABSTRACT

A transgenic mouse characterized by a lack of endogenous SPARC expression is provided. This mouse and tissue cultures derived therefrom provide useful models for testing drugs, particularly those useful in promoting or retarding wound healing and drugs useful for treating or preventing cataracts, diabetes mellitus, or osteoporosis. Also provided are methods of treating conditions characterized by overexpression or underexpression of SPARC.

27 Claims, 6 Drawing Sheets

PROBE: ☐ ⊢———⊣ 1KB

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 2079 base pairs
      (B) TYPE: nucleic acid
      (C) STRANDEDNESS: double
      (D) TOPOLOGY: unknown    (ii) MOLECULE TYPE: cDNA    (xi) SEQUENCE DESCRIPTION: SEQ ID NO: 1:

```
GCATTCCTGC AGCCCTTCAG ACCGCCAGAA CTCTTCTGCC GCCTGCCTGC CTGCCTGCCT      60
GCCTGCCTGT GCCGAGAGTT CCCAGCATCA TGAGGGCCTG GATCTTCTTT CTCCTTTGCC     120
TGGCCGGGAG GGCCCTGGCA GCCCCTCAGC AGACTGAAGT TGCTGAGGAG ATAGTGGAGG     180
AGGAAACCGT GGTGGAGGAG ACAGGGGTAC CTGTGGGTGC CAACCCAGTC CAGGTGGAAA     240
TGGGAGAATT TGAGGACGGT GCAGAGGAAA CGGTCGAGGA GGTGGTGGCT GACAACCCCT     300
GCCAGAACCA TCATTGCAAA CATGGCAAGG TGTGTGAGCT GGACGAGAGC AACACCCCCA     360
TGTGTGTGTG CCAGGACCCC ACCAGCTGCC CTGCTCCCAT TGGCGAGTTT GAGAAGGTAT     420
GCAGCAATGA CAACAAGACC TTCGACTCTT CCTGCCACTT CTTTGCCACC AAGTGCACCC     480
TGGAGGGCAC CAAGAAGGGC CACAAGCTCC ACCTGGACTA CATCGGACCA TGCAAATACA     540
TCGCCCCCTG CCTGGATTCC GAGCTGACCG AATTCCCTCT GCGCATGCGT GACTGGCTCA     600
AAAATGTCCT GGTCACCTTG TACGAGAGAG ATGAGGGCAA CAACCTCCTC ACTGAGAAGC     660
AGAAGCTGCG TGTGAAGAAG ATCCATGAGA ATGAGAAGCG CCTGGAGGCT GGAGACCACC     720
CCGTGGAGCT GTTGGCCCGA GACTTTGAGA AGAACTACAA TATGTACATC TTCCCTGTCC     780
ACTGGCAGTT TGGCCAGCTG GATCAGCACC CTATTGATGG GTACCTGTCC CACACTGAGC     840
TGGCCCCACT GCGTGCTCCC CTCATCCCCA TGGAACATTG CACCACACGT TTCTTTGAGA     900
CCTGTGACCT AGACAACGAC AAGTACATTG CCCTGGAGGA ATGGGCCGGC TGCTTTGGCA     960
TCAAGGAGCA GGACATCAAC AAGGATCTGG TGATCTAAGT TCACGCCTCC TGCTGCAGTC    1020
CTGAACTCTC TCCCTCTGAT GTGTCACCCC TCCCATTACC CCCTTGTTTA AAATGTTTGG    1080
ATGGTTGGCT GTTCCGCCTG GGGATAAGGT GCTAACATAG ATTTAACTGA ATACATTAAC    1140
GGTGCTAAAA AAAAAAAAA AACAAAGTAA GAAAGAAACT AGAACCCAAG TCACAGCATT    1200
TTCCCACATA ACTCTGAGGC CATGGCCCAT CCACAGCCTC CTGGTCCCCT GCACTACCCA    1260
GTGTCTCACT GGCTGTGTTG GAAACGGAGT TGCATAAGCT CACCGTCCAC AAGCACGAGA    1320
TATCTCTAGC TTTCATTTCA ATTTTGCATT TGACTCTTAA CACTCACCCA GACTCTGTGC    1380
TTATTTCATT TTGGGGGATG TGGGCTTTTT CCCCTGGTGG TTTGGAGTTA GGCAGAGGGA    1440
AGTTACAGAC ACAGGTACAA AATTTGGGTA AAGATACTGT GAGACCTGAG GACCCACCAG    1500
TCAGAACCCA CATGGCAAGT CTTAGTAGCC TAGGTCAAGG AAAGACAGAA TAATCCAGAG    1560
CTGTGGCACA CATGACAGAC TCCCAGCAGC CCGGGACCTT GCTGTCTTCT CGACTCTTCG    1620
GGCGTTTCTT TCCATGTTTG GCTGTTGGTT TTAGTTTTGG TGAGCCATGG GTGGGCCAGA    1680
ACATCACTCA ACTGCAATTG GGCTTTCAGG TTCTTGCCGG GAGCTCTAGG CACTGGGAGG    1740
CTGTTTCAGG AAAGTGAGAC TCAAGAGGAA GACAGAAAAG GTTGTAACGT AGAGGAAGTG    1800
```

-continued

```
AGACTGGTGA ATTGGTTTGA TTTTTTTCAC ATCTAGATGG CTGTCATAAA GTTTCTAGCA    1860

TGTTCCCCCT CACCTCTCCC CACCCCCTGC CACTTGAAAC CTTCTACTAA TCAAGAGAAA    1920

CTTCCAAGCC AACGGAATGG TCAGATCTCA CAGGCTGAGA AATTGTTCCC CTCCAAGCAT    1980

TTCATGAAAA AGCTGCTTCT CATTAACCAT GCAAACTCTC ACAGCGATGT GAAGAGCTTG    2040

ACAAGTCTTT CAAAATAAAA AGTAACAACT TAGAAACGG                           2079
```

SPARC-DEFICIENT TRANSGENIC MICE

CROSS-REFERENCE TO RELATED APPLICATIONS

This is a 371 of PCT/US97/20320, which claims the benefit of the priority of U.S. patent application Ser. No. 60/030,572, filed Nov. 7, 1996.

This was supported by grant GM37762 from the National Institute of General Medical Sciences. The U.S. government has certain rights in this invention.

FIELD OF THE INVENTION

This invention relates generally to genetically altered non-human animals, and particularly, to knockout animals, i.e., animals lacking a native gene function.

BACKGROUND OF THE INVENTION

SPARC (secreted protein acidic and rich in cysteine), also known as osteonectin and BM-40, is an extracellular matrix (ECM)-associated glycoprotein widely distributed in human and murine tissues undergoing developmental regulation. While its specific role remains elusive, the high degree of interspecies conservation suggests a strong evolutionary pressure to conserve this protein. Extensive studies thus far have implicated SPARC in diverse functions including cell proliferation [Lane and Sage, *FASEB J.*, 8:163–173 (1994)].

ECM proteins are required for growth factor stimulated cell proliferation since anchorage dependent cells grown as suspension cultures in the absence of ECM die eventually. However, the role of individual ECM proteins to support the growth induced by individual growth factor is not known. SPARC has been shown to influence cell growth in a cell type-specific manner. Down-regulation of SPARC did not perturb melanoma cell growth, while over-expression in ovary cancer cell lines or addition of purified SPARC to endothelial cells retarded cell growth [Ledda et al, *Nature Med.*, 3:171–176, (1997); Mok et al., *Oncogene*, 12:1895–1901 (1996); Funk and Sage, *J. Cell. Phsiol.*, 154:53–63 (1993)]. Nevertheless, peptides corresponding to SPARC domain II stimulate cell proliferation [Funk and Sage, *J. Cell. Physiol.*, 154:53–63 (1993)]. This result strongly suggests that extracellular cleavage may have important consequences on the ability of SPARC to modulate cell growth. Furthermore, SPARC was shown to interact with growth factors, cytokines and ECM components [Lane and Sage, *FASEB J.*, 8:163–173 (1994)], indicating that SPARC may profoundly influence cell growth through these diverse functions.

The role of SPARC in cell proliferation is further supported by its expression in sprouting endothelial cells and endothelial cords during angiogenesis and in fibroblasts and macrophages migrating into wound sites [Sage and Bornstein, *J. Biol. Chem.*, 266:14831–14834 (1991); Reed et al., *J. Histochem. Cytochem.*, 41:1467–1477 (1993)]. Moreover, SPARC is highly expressed in actively dividing osteoblasts, hypertrophic chondrocytes at growth plates and in developing embryos [Lane and Sage, cited above].

SPARC is abundantly expressed in extraembryonic parietal endoderm [Mason et al, *EMBO J.*, 5:1465 (1986)], which specializes in the synthesis and secretion of a thick basement membrane known as Reichert's membrane or the parietal yolk sac. This membrane acts as a barrier keeping embryonic fluid inside to provide nutrients to embryos and to protect embryos from outside shock. SPARC is expressed in the heart, lung and somites of embryos. Somites differentiate into vertebrae, ribs, muscles and dermis of skin. Transgenic nematodes over-expressing SPARC are abnormal. Embryos are deformed, and adults show reduced mobility and paralysis, suggesting the involvement of SPARC in the adhesion of muscle cells to the ECM [Schwarzbauer and Spencer, *Mol. Biol. Chem.*, 4:941–952 (1993)]. Microinjection of SPARC antibodies into Xenopus embryos resulted in abnormal axial development and developmental arrest at the neurula and tailbud stages [Purcell et al., *J. Exp. Zool.*, 265:153–164 (1993)].

There is a need in the art, especially in the medical and pharmaceutical fields, for commercial research and diagnostic systems useful for testing cell proliferation and screening for diseases resulting from impaired cell proliferative processes.

SUMMARY OF THE INVENTION

In a first aspect, the invention provides a fertile, transgenic non-human mammal having a phenotype characterized by the substantial absence of SPARC. This mammal is preferably a mouse. The transgenic animals of the invention provides a system useful for screening age-related conditions such as impaired wound healing, cataracts, diabetes mellitus, nephropathy and osteoporosis.

In another aspect, the invention provides a method for producing a transgenic non-human mammal having a phenotype characterized by the substantial absence of SPARC otherwise naturally occurring in the animal. This method involves introducing a transgene into an embryonic stem cell which disrupts the function of the native SPARC gene; injecting the cell into a blastocyst; transplanting the blastocyst into a pseudopregnant mammal; allowing the embryo to develop to term; identifying at least one transgenic offspring containing the transgene; and breeding said offspring to form a transgenic SPARC deficient animal having the phenotype.

In yet another aspect, the present invention provides a recombinant mammalian cell containing a transgene which causes a disruption in the function of SPARC.

In still another aspect, the present invention provides a method for screening drugs useful for the treatment of impaired wound healing, cataracts, diabetes mellitus, nephropathy and osteoporosis by utilizing the SPARC-deficient transgenic non-human mammals of the invention or cell cultures derived therefrom.

In yet another aspect, the present invention provides compositions and methods for modulating SPARC expression. These methods include use of polynucleotide molecules, such as viral and plasmid vectors, containing SPARC polynucleotide sequences.

Other aspects and advantages of the present invention are described further in the following detailed description of the preferred embodiments thereof.

BRIEF DESCRIPTION OF THE DRAWINGS

FIG. 1A provides the structure of the SPARC gene, with only relevant restriction sites shown. B indicates BamHI; H indicates HindIII, N indicates NsiI. Locations of exons 2 to 5 are indicated. The expected length of a restriction fragment diagnostic for homologous recombination is shown.

FIG. 1B provides the structure of the targeting vector, in relationship to the SPARC gene of FIG. 1A, as described in Example 1. Horizontal arrows indicate the direction of transcription of the neo and TK expression cassettes.

FIG. 1C provides the predicted structure of the targeted locus following homologous recombination, in relationship to the SPARC gene (FIG. 1A) and targeting vector (FIG. 1B). See Example 1. Expected lengths of restriction fragments diagnostic for homologous recombination are shown.

DETAILED DESCRIPTION OF THE INVENTION

The present invention provides a transgenic non-human mammal containing a functional disruption in the SPARC allele native to the mammal, i.e., containing a SPARC null mutation. A preferred transgenic non-human mammal is a mouse, which is exemplified herein. In view of the fact that the literature described SPARC as having functions in embryogenesis, it was anticipated that mice lacking SPARC would be sterile and embryonically lethal. Thus, it was unexpected that these transgenic mice would be both viable and fertile. Further, the transgenic mice of the invention have been found to develop subtle phenotypes over their life time such as impaired wound healing and age related dysfunction characterized by cataracts, diabetes, proteinuria, and osteoporosis, as described in more detail below. Thus, these transgenic animals provide a useful model for testing drugs, particularly drugs with indications for promoting or retarding wound healing and drugs for treatment or prevention of cataracts, diabetes mellitus, or osteoporosis.

As used herein, the term "transgenic animal" refers to all mammals, except humans, bearing genetic information, i.e., a "transgene", received, directly or indirectly, by deliberate genetic manipulation at a subcellular level. For convenience, the following discussion will refer to transgenic mice. However, it should be understood that other non-human mammals can be similarly used. As used herein, a "transgene" is a DNA sequence introduced into the germ line of a non-human animal by way of human intervention, such as by the methods described herein. The transgene includes disrupted SPARC DNA sequences which are capable of suppressing endogenous SPARC alleles.

These transgenic animals include animals in which the genetic information was introduced into a germ line cell, thereby conferring the ability to transfer the transgene to offspring. Also encompassed within this invention are methods of obtaining a null SPARC non-human animal, preferably a mouse, by using classical breeding techniques, or in vitro fertilization, with a transgenic null SPARC animal, as defined above. Thus, offspring of the transgenic animals described herein are also provided.

Production and Characterization of SPARC-Deficient Transgenic Non-Human Animals

Methods for producing transgenic animals are known to those of skill in the art. The currently preferred method for producing a transgenic SPARC deficient animal of the invention is the embryonal stem cell (ES) method. ES cells are obtained from pre-implantation embryos and cultured in vitro [Evans et al, Nature, 292:154–156 (1981)]. Transgenes can be efficiently introduced into the ES cells by DNA transfection. Such transformed ES cells can thereafter be combined with blastocysts from a non-human animal. The ES cells then colonize the embryo and contribute to the germ line of the resulting chimeric animal. See, R. Jaenisch, Science, 24:1468–1474 (1988).

The transgenic mice of the invention were produced as described in detail in Example 1. Briefly, the transgene contains a neomycin resistant gene which disrupts the coding sequence of the SPARC gene. Replacement of the endogenous SPARC gene by the transgene via homologous recombination in ES cells derived from 129 mice will give rise to cells with mutation in the desired allele. These heterozygotes are injected into C57BL/6 blastocysts and resulting blastocysts introduced into the uterine horns of pseudopregnant mice. Chimeric mice, with agouti coat color derived from 129 ES cells and black coat color from C57BL/6 blastocysts were identified and back-crossed to C57BL/6 mice. Agouti offspring were generated from fertilization of ES cells derived and C57BL/6 derived germ cells since agouti coat color is dominant over black coat color. Agouti offsprings were then screened for germline transmission of the targeted mutation. The heterozygous SPARC mutant mice were then inter-crossed to generate homozygous mutant mice (SPARC-deficient transgenic mice).

As stated above, the inventor unexpectedly found that the SPARC-deficient transgenic mice of the invention are both viable and fertile. In addition, these mice have been found to be characterized by certain phenotypes. More particularly, as described in Examples 2 and 3, the inventor has investigated DNA synthesis of embryonic fibroblasts derived from the SPARC-null transgenic mice of the invention in a synthetic medium containing insulin. Insulin, a hormone affecting multiple cellular processes, rapidly regulates short-term effects on carbohydrate, lipid and protein metabolism and is also a potent growth factor controlling cell proliferation and differentiation. The inventor shows herein that growth factor insulin-mediated DNA synthesis in SPARC-null fibroblasts derived from the transgenic mice of the invention was depressed as compared to wild-type control cells. Consistently, insulin-induced cell cycle regulated genes was repressed. Most importantly, as insulin mediates the majority of its mitogenic action through the IGF-1 receptor

[Rodeck et al., *Int. J. Cancer*, 40:687–690 (1987)], the inventor has found that expression of IGF-1 receptor mRNA was decreased in SPARC-null cells of the invention. Thus, the synergistic action of SPARC and insulin/IGF-1 (insulin growth factor-1) is needed for normal cell proliferation.

The in vitro data prompted the inventor to investigate wound healing since this process involves cell proliferation. See, Example 4 below. Re-epithelialization in SPARC-null transgenic mice of the invention has been found to progress normally at cutaneous wound sites, but granulation and wound closure was significantly delayed compared to wild-type controls. This impaired wound healing process is likely due to the decreased growth promoting action of insulin/IGF-1 resulting from the low levels of IGF-1 receptor mRNA at the wound sites. These mice also develop senile cataracts which is known to result from insulin mediated glucose metabolic derangement. See Example 5. Consistently, early results indicate that these mice also manifest hyperglycemia, proteinuria, and osteopenia late in their lives. See Examples 6 and 7 below. Such secondary lesions are common in diabetes mellitus patients suffering from the same derangement. Further, contact x-rays of a set of 8 month old mice of the invention showed that the transgenic mouse was osteopenic.

Use of SPARC-Deficient Transgenic Animals

The transgenic animals of the invention, lacking SPARC activity, have a variety of uses which include research uses for diabetes-related conditions, conditions associated with over-expression of corticosteroids, and research related to solid tumor growth. Another suitable use includes screening for drugs useful in treating these and associated conditions.

For example, the SPARC-deficient transgenic mice exemplified herein have a decreased ability to heal wounds largely due to impaired mitogenic action of insulin/IGF-1 and, thus, reduced DNA synthesis. These transgenic mice also develop senile cataracts. Preliminary results indicate that the mice develop hyperglycemia, proteinuria, and osteopenia late in life. All these phenotypes are common complications of diabetes: diabetics suffer from retarded wound healing, cataract formation, hyperglycemia, proteinuria, and osteopenia. While hereditary influences are known to contribute significantly to the development of diabetes, genes associated with this disease have not yet been identified. Therefore these mice are useful for diabetes-related research. Similarly, transgenic SPARC deficient mice are useful in investigating the effect of SPARC-null mutation on corticosteroid production. SPARC is abundantly expressed in the adrenal glands which produce corticosteroids. Patients under corticosteroid therapy develop chronic wounds, cataracts, hyperglycemia (diabetes), and osteoporosis. Analysis of the corticosteroid hormone levels in SPARC-null mice will reveal whether SPARC-deficiency contributes to over-expression of the hormones which in turn lead to the disorders. These transgenic SPARC deficient animals (and particularly mice) are also useful systems for study of solid tumor growth and arthritis.

The transgenic animals of the invention are particularly well suited for testing compounds designed to modulate (i.e., augment or reduce) SPARC expression, and to treat diabetic retinopathy, wound healing, cataracts, hyperglycemia, nephropathy, proteinurea, and osteoporosis, among a variety of other conditions, which will be readily apparent to those of skill in the art. The test compounds may be biologicals, including polynucleotide- and protein-based therapeutics, chemical compounds, or combinations thereof. In a particularly desired embodiment, the transgenic animals of the invention are suitable for use as a model for testing gene therapy vectors which may be used to deliver a desired polynucleotide sequence. Such polynucleotide sequences include those which modulate SPARC expression and are discussed in more detail below.

Methods of using animals for screening test compounds are well known. For example, one could make an incision in transgenic mice of the invention, administer a test compound or formulation to a subset of the transgenic mice bearing the wound, and compare the results, e.g., wound healing, in the test group to wound healing in a subset of the mice which serves as a control group.

The SPARC-deficient transgenic animals of the invention can also be used as a source of cells for cell culture. Cells of tissues carrying the null mutation can be cultured, by standard tissue culture techniques, and used for a variety of purposes which will be readily apparent to those of skill in the art. As one example, these tissue cultures may be useful for screening test compounds, as described above.

Constructs for Modulating SPARC Expression

Suitable constructs for delivery of a polynucleot:ide sequence to a selected host cell, and particularly, mammalian cells, are well known in the art. As described herein, under certain circumstances it is desirable to deliver to a cell polynucleotide sequences, i.e., anti-sense DNA, which suppress or reduce SPARC expression in the cell. Under another set of circumstances it is desirable to deliver to a cell polynucleotide sequences which increase SPARC expression in the cell, i.e., SPARC coding or sense sequences. These polynucleotide molecules contain sequences derived from SPARC which may be in the form of RNA, such as mRNA, or in the form of DNA, including, for example, cDNA and genomic DNA obtained by cloning or produced by chemical synthesis techniques or by a combination thereof. The DNA may be double-stranded or single-stranded. Single-stranded DNA may be the non-coding strand, also known as the anti-sense strand.

SPARC polynucleotide sequences are known and may be readily obtained from a variety of sources, including Gen-Bank. One suitable SPARC sequence is described in Mason et al, *EMBO J.*, 5:1465–1472 (1986); this sequence is also available from GenBank (accession number X04017) and is reproduced herein as SEQ ID NO:1. Currently, it: is preferred that the SPARC polynucleotides correspond to SEQ ID NO:1, the strand complementary thereto, or fragments thereof. Suitable fragments include sequences encoding biologically active fragments of SPARC, or anti-sense sequences of sufficient length to disrupt SPARC expression or overexpression in the host cell. The skilled artisan can readily determine suitable SPARC sense and anti-sense fragments. In addition, variants may be readily made or obtained by one of skill in the art. For example, one suitable variant is a fusion molecule containing the SPARC sequences linked to a fusion partner for a desired purpose, e.g., improving expression in the host cells. Such fusion partners may be readily selected from glutathionine reductase (GST) and the influenza non-structural protein NS1, among others which are known to the skilled artisan. Another suitable variant of the SPARC sequences involves genetically engineered replacement of preference codons using known techniques to improve expression in the selected host cell. Yet another variant of the SPARC sequences of SEQ ID NO:1, includes natural allelic variants, e.g., SPARC sequences from another mammalian species.

Molecules for delivery of the SPARC polynucleotide sequences (either coding strand or anti-sense strand) may be readily constructed by one of skill in the art. Such molecules include viral vectors, which are well known for delivery of polynucleotide sequences to mammalian cells. Examples of suitable viral vectors include, e.g., retroviruses, vaccinia viruses, poxviruses, adenoviruses and adeno-associated viruses, among others. The selection of the virus used to construct the recombinant vector useful in the present invention, including the viral type, e.g., adenovirus, and strain does not limit the following invention. Similarly, selection of the regulatory sequences, e.g., promoters, enhancers, termination sequences, and the like, which direct expression of the SPARC polynucleotide sequences and are operably linked thereto, do not limit the present invention. Other suitable polynucleotide molecules include DNA molecules, in which the SPARC polynucleotide sequences are linked to promoters and other conventional regulatory sequences directing expression thereof in the host cell. Thus, the SPARC polynucleotide sequence may be administered as so-called "naked DNA". See, e.g., J. Cohen, *Science*, 259:1691–1692 (Mar. 19, 1993); E. Fynan et al, *Proc. Natl. Acad. Sci. USA*, 90:11478–11482 (December 1993); and J. A. Wolff et al, *Biotechniques*, 11:474–485 (1991). Optionally, these SPARC sequences are inserted into a suitable plasmid for delivery to a host cell. Such plasmid vectors may be obtained from a variety of commercial and academic sources, or may be constructed using known techniques.

In one embodiment, the invention provides a polynucleotide molecule which is useful for treatment of such solid tumors as melanoma, breast cancer, or colorectal cancer and for reducing over-growth of vasculatures in joints associated with arthritis. This vector construct for eliminating or reducing native SPARC function or overexpression of SPARC contains SPARC anti-sense cDNA sequences, e.g., the sequences complementary to those provided in SEQ ID NO:1, or fragments thereof which have similar activity.

Another gene therapy vector according to the invention is capable of delivering SPARC to cells of a veterinary or human patient having a condition characterized by under-expression of SPARC. Such conditions may include diabetes, osteoporosis, cataracts, and other age-related conditions, which have been described herein. Suitably, the SPARC gene, or fragment thereof characterized by SPARC's biological activity, is delivered via a polynucleotide molecule containing the polynucleotide sequences encoding SPARC or the SPARC fragment.

Suitably, the polynucleotide molecules of the invention may be formulated for administration to a patient, or used in vitro, as discussed herein.

Use of Mammalian Cells Containing Polynucleotide Molecules of the Invention and Methods of Modulating SPARC Expression The invention further provides a method of providing mammalian cells with a functional deletion or disruption of the native SPARC allele. In a preferred embodiment, the mammalian cells are transformed with the anti-sense SPARC cDNA. These mammalian cells may be human or non-human in origin. These cells may be used in vitro for a variety of purposes. Alternatively, the recombinant mammalian cells of the invention may be introduced (or re-introduced) into a mammalian host in an amount sufficient to achieve a desired therapeutic or prophylactic effect, e.g., about $10^2$ to $10^{13}$ cells/kg. In still another alternative, the mammalian cells may be infected or transfected in vivo with 1 μg to 10 mg of the polynucleotide construct containing anti-sense SPARC cDNA per kg body weight, in order to reduce SPARC expression. Where recombinant viral vectors are utilized for delivery of the SPARC DNA, vectors are desirably administered in amount between $1 \times 10^7$ to $1 \times 10^{10}$ pfu virus/ml. These cells, this DNA, or the viral vectors may be suspended in a physiologically compatible pharmaceutical carrier (e.g., saline or the like) and administered by any suitable route, e.g., intravenous, intramuscular. Suitable carriers and routes of administration may be readily determined by one of skill in the art. A preferred dose is between 1 to 10 ml of a selected carrier at the above concentrations. These ex vivo and in vivo methods and compositions of the invention are useful for treating conditions associated with over-production of SPARC, including, e.g., solid tumors and arthritis.

Similar methods may be utilized to treat conditions associated with under-expression of SPARC, e.g., diabetes, osteoporosis, proteinurea, cataracts, utilizing the polynucleotide constructs which direct expression of SPARC, described above. Suitably, prior to administration of a vector directing expression of SPARC, the patient having a condition believed to be associated with a SPARC deficiency (e.g., diabetes) is screened to determine SPARC levels. Such a screening may be performed utilizing known methods, e.g., by obtaining a sample from a veterinary or human patient, and utilizing anti-SPARC antibodies to determine the SPARC levels by immunoprecipation, Western blot, or by other suitable means, many of which are known to the skilled artisan. These results are then compared to a standard which may be readily determined by screening one or more healthy patients to determine a normal SPARC range. For those patients determined to have a SPARC deficiency by comparison to a standard such as that described above, their conditions may be treated by administering a vector which permits expression of SPARC in the cells of the patient. Suitable amounts of these vectors may be readily determined by one of skill in the art and, in general, are in accordance with the doses and routes of administration described above in connection with the delivery of anti-sense SPARC cDNA.

Optionally, it may be desirable to administer the polynucleotide molecules of the invention, which contain SPARC polynucleotide sequences, in conjunction with an immunosuppressant, or with other conventional therapies. In another embodiment, it may be desirable to administer the polynucleotide molecules of the invention which direct expression of SPARC in conjunction with insulin and/or IGF-1. Insulin/IGF-1 may be obtained from commercial sources, or produced using known techniques.

These examples illustrate the preferred methods for preparing the transgenic mouse of the invention. These examples are illustrative only and do not limit the scope of the invention.

EXAMPLE 1

Generation of Transgenic Mouse

Figure 1A:
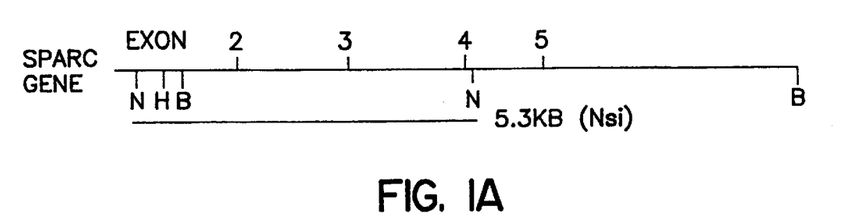

Briefly, an exemplary transgenic non-human animal of the invention was generated as follows. The SPARC locus in mouse ES cells was disrupted using the positive-negative selection method [Mansour et al., *Nature*, 336:348–352 (1988)]. The targeting vector was constructed from a 9.3-kb fragment encompassing exons 2 to 5 of the mouse SPARC gene (FIG. 1A). Exon 4 was disrupted by insertion of the neomycin resistance genes pMClneo and pPol2neo. A HSV-TK gene was also added to the 3' end of the SPARC genomic fragment to allow counter-selection against random integration, therefore enriching homologous recombination events. Upon electroporation of the targeting constructs into ES cells, G418- and gancyclovir-resistant clones were selected, expanded, and screened for homologous recombination events by Southern hybridization. A targeted ES clone was then injected into C57BL/6 mouse blastocysts and male chimeras were subsequently mated with C57BL/6 females to identify ES cell-derived offspring with the dominant agouti coat color. Heterozygous offspring were identified by Southern analysis. Both male and female heterozygotes were healthy and fertile and were inter-crossed to generate homozygotes, i.e., SPARC-deficient transgenic mice. These methods are described in detail in A.–C. below.

A. Construction of Targeting Vector

Figure 1B:
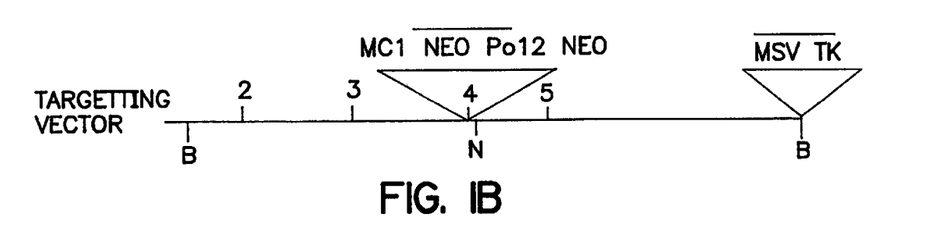
Figure 1C:
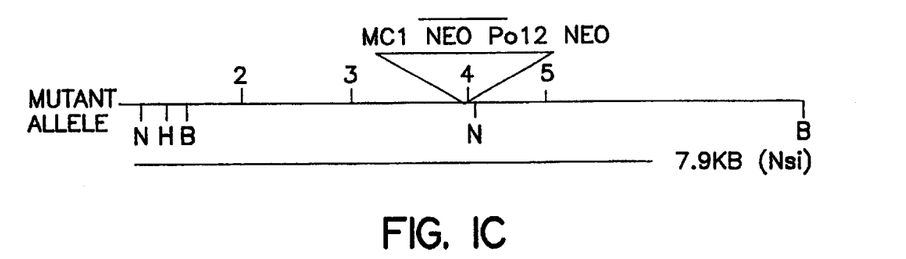
Figure 1D:
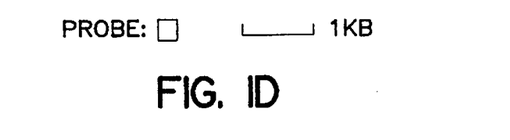
FIG. 1D provides the identity of the probe, and the scale bar (1 kb) used in FIGS. 1A–1C. See Example 1.

The SPARC genomic DNA clone was isolated from a 129/SV mouse liver DNA cosmid library in pcos2EMBL [Poustka et al., *Proc. Natl. Acad. Sci.*, 81:4129–4133 (1984)] by screening with a mouse cDNA probe consisting of nucleotide numbers 33 to 729 of SEQ ID NO:1 [Howe et al., *Differentiation*, 37;20–25 (1988)]. A 6.3 kb BamHI fragment containing exons 2 to 5 of the SPARC gene [McVey et al, *J. Biol. Chem.*, 263:11111–11116 (1988)] was cloned into plasmid puc19 [GIBCO BRL], and two neomycin-resistant gene expression cassettes, pMCIneo and modified pPol2sneobpA [Thomas and Capecchi, *Cell*, 51:503–512 (1987); Soriano et al., *Cell*, 64:693–702 (1991)], were inserted at the beginning of exon 4 to enhance neomycin resistance (see FIGS. 1A–1D). A 3-kb BamHI fragment containing SPARC intron 5 was cloned into puc19, and the pMCl-herpes simplex virus-thymidine kinase (HSV-TK) construct [Mansour et al., *Nature*, 336:348–352 (1988)] was inserted at the 3' end of the genomic fragment. The 3-kb BamHI construct was then fused to the 3' end of the 6.3-kb BamHI fragment in correct orientation. The resulting construct, termed pSPARC2-5neo/TK, is illustrated in FIG. 1B, and is the targeting vector used to transfect the ES cells, as described below. As stated above, this construct has been deposited pursuant to the Budapest Treaty with the American Type Culture Collection, 12301 Parklawn Drive, Rockville, Md. (USA), on Nov. 8, 1995 and granted Accession Number 97335.

B. Cell Cultures and Transfections

CCE ES cells derived from 129/SV mouse embryos were routinely cultured on G418 resistant STO feeder cells [ATCC] in Dulbecco's modified Eagle's medium containing 10% fetal bovine serum (FBS) and conditioned medium (10%) from CV-1 cells transfected with a LIF expression construct to inhibit differentiation of ES cells [Williams et al., *Nature*, 336:684–687 (1988)]. Cells were trypsinized, resuspended at a concentration of $1 \times 10^7$ cells per ml in electroporation buffer (phosphate-buffered saline containing 10 mM Hepes, pH 7.4), mixed with 20 µg of the linearized targeting vector, incubated on ice for 10 minutes, and electroporated with a Bio-Rad Gene Pulser at room temperature at 220 V, 960 µF. Cells were allowed to recover on ice for 10 minutes and at room temperature for 10 minutes, and then seeded with STO cells on 10 cm plates. Forty-eight hours after transfection, cells were selected with 100 µg/ml G418 (active form, GIBCO) and 2 µM gancyclovir [Syntex] for 10 days. Drug-resistant colonies were picked and expanded on STO feeder layers without further drug selection. DNA was isolated [Hogan et al., *Manipulating the Mouse Embryo. A Laboratory Manual*, Cold Spring Harbor, New York: Cold Spring Harbor Press (1986)] and tested for the presence of a disrupted SPARC gene by Southern analysis. NsiI digestion of genomic DNA yielded a wild-type allele of 5.3 kb and a mutant allele of 7.9 kb (see FIGS. 1A and 1C). The frequency of homologous recombination was $2 \times 10^{-8}$ per electroporated cell.

C. Generation of Chimeras

ES cells carrying the disrupted SPARC gene were injected into C57BL/6 blastocyst stage embryos to generate chimeras. One chimera was then mated to C57BL/6 mice, and tail DNA from agouti mice was isolated [Hogan et al., cited above, 1986] for genotype analysis by Southern hybridization. Heterozygous SPARC mutant mice were inter-crossed to generate wild-type (+/+), heterozygous (+/−), and homozygous (−/−) SPARC mutant mice (SPARC-deficient transgenic mice). The wild-types and homozygotes were separately interbred for subsequent experiments.

Genotyping of litters after weaning at 4 weeks of age showed a Mendelian distribution of wild-type (+/+), heterozygous (+/−), and homozygous mutant (−/−) mice (Table 1).

TABLE 1

| Cross | Age (weeks) | Homozygous Wild-Type (+/+) | Heterozygous (+/−) | Homozygous (−/−) |
|---|---|---|---|---|
| (+/−) × (+/−) | 4 | 28 | 43 | 37 |

Total RNA from wild-type, heterozygous and homozygous mice for the disrupted SPARC allele was isolated by the sodium dodecyl sulfate/hot phenol method and analyzed by Northern hybridization using a SPARC cDNA probe containing the 5' most sequence of SPARC mRNA [nucleotides 1 to 600 using the numbering system of Mason et al, *EMBO J.*, 5:1465–1472 (1986), SEQ ID NO:1]. As a control for RNA loading, blots were reprobed with mouse elongation factor 2 (EF-2) CDNA which encodes the housekeeping gene product, EF-2 which is involved in peptide chain elongation in eukaryotes. SPARC mRNA was abundant in testis of heterozygotes, but it was not detectable in testis of homozygotes. The level of transcript in thymus and brain of wild-type and heterozygotes was low, while absent from mutants. The transcript levels in spleens of heterozygotes also showed decrease from wild-type.

Embryonic fibroblasts derived from homozygous mutant mice and wild-type mice were labeled with [$^{35}$S]methionine, and cell lysates and culture media were immunoprecipitated and analyzed by sodium dodecyl sulfate-polyacrylamide gel electrophoresis (SDS-PAGE). This analysis indicated that SPARC is synthesized and secreted by wild-type cells, but not by homozygotes (transgenic mice).

D. Anatomical and Histological Analysis

Radiographs and gross necropsies of three 3-month-old litter mates (homozygous, heterozygous, and wild-type) were performed. Tissues from these mice were isolated, fixed in buffered Formalde Fresh (Fisher), embedded in paraffin, sectioned and stained with hematoxylin and eosin for morphological analysis.

SPARC-deficient transgenic mice (homozygotes) were indistinguishable from heterozygous or wild-type mice in growth, fertility, and viability even after several generations of inter-crossing. Necropsy revealed no significant differences in the tissue weights of liver, spleen, kidney, heart, and brain between wild-type and homozygous mice. Although SPARC has been implicated in bone development, radiographic analysis indicated no obvious pathological changes in the bone structure of transgenic mice as compared to that of heterozygous or wild-type mice. Histological examination of femur, tibia, and knee joint not only substantiated the radiographic data, but also indicated that the hypertrophic chondrocytes at the growth plates, where SPARC expression is high, were normal. Basement membranes of renal glomeruli of transgenic mice also appeared histologically normal, despite previous reports of SPARC's association with the basement membrane during development [Mason et al., *EMBO J.*, 5:1465–1472 (1986); Lane and Sage, *FASEB J.*, 8:163–173 (1994)]. The liver was also essentially normal by histology.

Although the SPARC-null transgenic mice of the invention are viable and fertile, they develop subtle phenotypes over their life time such as impaired wound healing, cataracts, and possibly hyperglycemia, diabetes, proteinuria, and osteopenia late in life indicating insulin mediated metabolic dysfunction.

EXAMPLE 2

Expression of Embryonic Fibroblasts

To assess possible defects in cell proliferation assembly by SPARC-deficient transgenic mice prepared according to Example 1, the DNA synthesis of embryonic fibroblasts was analyzed as follows.

Figure 2:
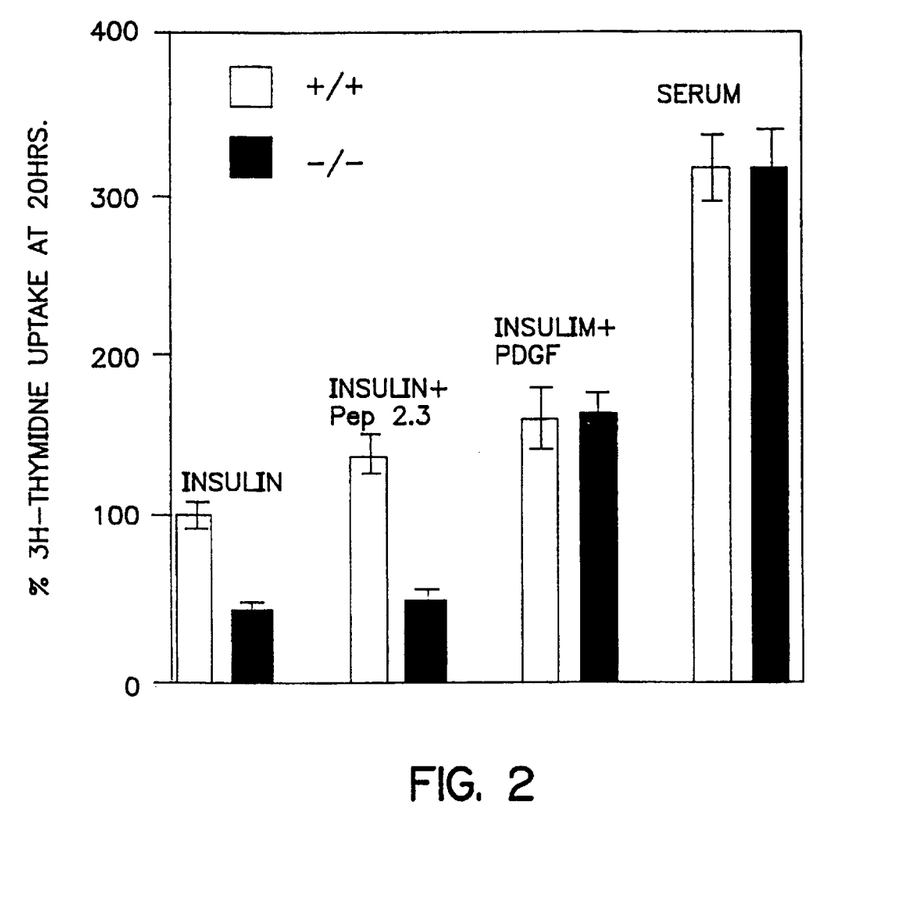
FIG. 2 provides a graph of incorporation of $^3$H-thymidine by SPARC-null (−/−) and wild type (+/+) embryonic fibroblasts at 20 h post-stimulation with insulin, or insulin plus peptide 2.3, or insulin plus platelet-derived growth factor (PDGF)-AB or serum.

Primary embryonic fibroblasts [Robertson, "Embryo-derived stem cells", in *Teratocarcinomas and Embryonic Stem Cells, A Practical Approach* (ed. E. J. Robertson), pp. 77–78 (1987)] were prepared from embryos at 13.5 days of gestation (the day of copulation plug is 0.5) and DNA synthesis examined by [$^3$H]-thymidine incorporation. In all experiments, wild-type and SPARC-null embryonic fibroblasts were compared at identical passage numbers (<8). Cells were plated at low density ($1 \times 10^4$ cells) in 96-well plates and cultured overnight in DMEM containing 10% FBS followed by 24 h culture in DMEM without FBS. These FBS-depleted cells were then cultured in the presence of [$^3$H]thymidine (1 mCi/ml) in AIM-V medium [DMEM containing human serum albumin, transferrin, and insulin (2 µg/ml) (GIBCO)] or AIM-V medium containing recombinant platelet-derived growth factor (PDGF)-AB (10 ng/ml, GIBCO) or SPARC peptide 2.3 [0.05 mM, Funk and Sage, *J. Cell. Physiol.*, 154:53–63 (1993)], or DMEM containing 10% fetal bovine serum (FBS). After various times of labeling, cells were removed by a cell harvester (Tomtec) and radioactivity was measured in a cell harvester counter (Packard). Incorporation of the radiolabel by SPARC-null cells was 60% lower than by wild-type cells after 20 h stimulation with insulin (IGF-1) (FIG. 2). However, when cells were labeled with [$^3$H]thymidine in AIM-V medium supplemented with PDGF, the uptake of radiolabel by SPARC-null cells was comparable to that of control cells (FIG. 2). FBS, which contains numerous growth factors including insulin and PDGF, restored full DNA synthetic capacity of SPARC-null cells, whereas insulin combined with SPARC peptide 2.3, which contains amino acid sequences of the growth factor GHK and stimulates cell proliferation [Funk and Sage, *J. Cell. Physiol.*, 154:53–63 (1993)], was ineffective (FIG. 2). These results show that SPARC is needed for the cell growth promoting function of insulin.

EXAMPLE 3

Expression of Cell Cycle Regulated Genes and IGF-1 Receptor Gene

Figure 3:
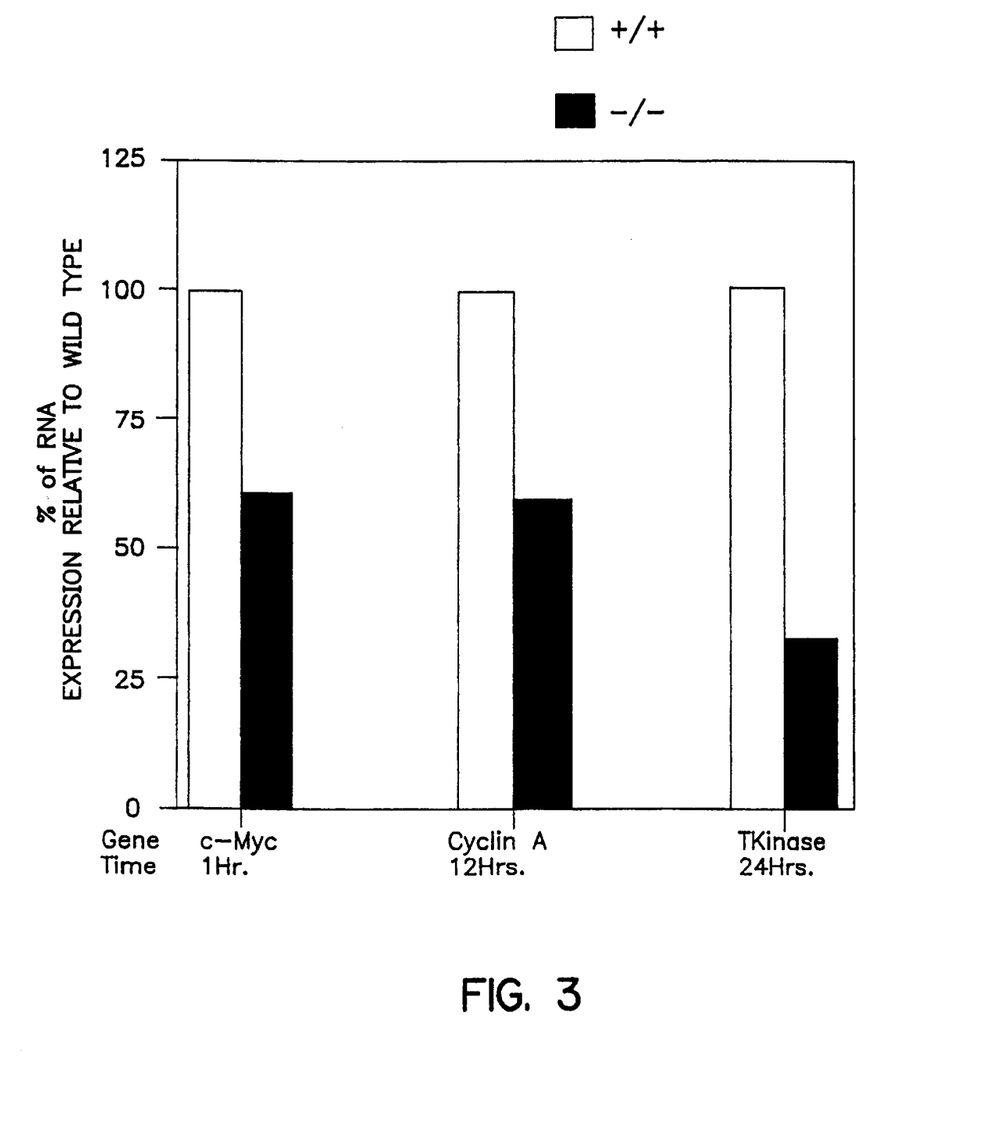
FIG. 3 provides a graph of expression of cell cycle regulated c-myc, cyclin A and thymidine kinase mRNA by SPARC-null embryonic fibroblasts (−/−) and wild-type cells (+/+). Transcription of c-myc gene peaked at 1 h after insulin stimulation, of cyclin A gene at 12 h after insulin stimulation and of thymidine kinase gene at 24 h post-insulin stimulation.

DNA synthesis in a cell is facilitated by cell cycle regulated genes such as c-myc, cyclin A and thymidine kinase [Avruch et al, *Trends Biochem. Sci.*, 19:279–283 (1994); Daksis et al., *Oncogene*, 9:3635–3645 (1994); Sherr, *Science*, 274:1672–1677 (1996)]. To analyze expression of these genes in SPARC-null embryonic fibroblasts, cells were plated at low density and cultured overnight in DMEM containing 10% FBS followed by 72 h culture in DMEM without FBS. These FBS-depleted cells were then cultured in AIM-V medium which contains insulin as the sole growth factor. At different times after insulin stimulation, cells were harvested and RNA was isolated. Northern hybridization showed that expression of c-myc, cyclin A and thymidine kinase mRNAs in the SPARC-null embryonic fibroblasts stimulated with insulin is compromised as compared to the wild type control cells (FIG. 3).

Figure 4:
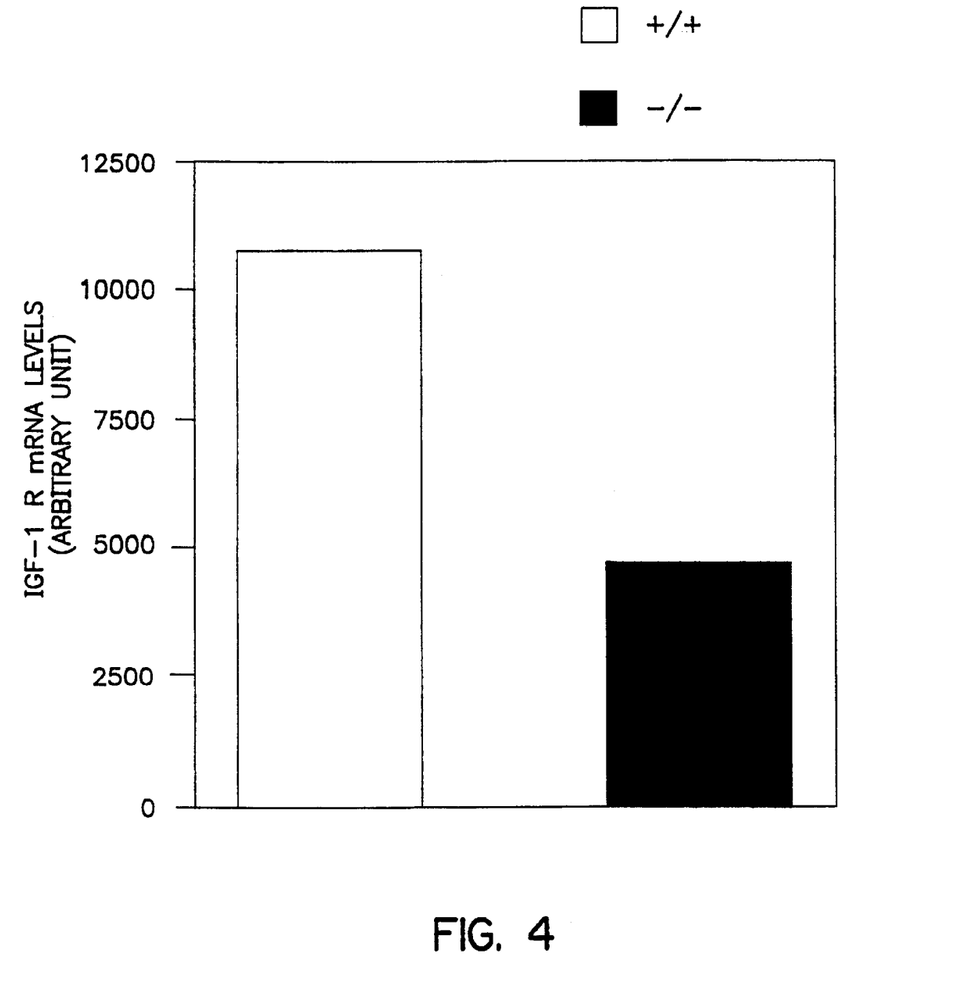
FIG. 4 provides a graph of expression of insulin-like growth factor-1 (IGF-1) receptor mRNA by SPARC-null embryonic fibroblasts (−/−) and wild-type cells (+/+).

Insulin mediates a weak mitogenic response through its own receptor and a strong response through IGF-1 receptors [Ulrich et. al., *Int. J. Cancer*, 40:687–690 (1987)]. Expression of the IGF-1 receptors was examined in embryonic fibroblasts by Northern hybridization with a probe containing the human IGF-1 receptor precursor [Ullrich et. al., *EMBO J.*, 5:2503–2512 (1986)]. It was found that the receptor mRNA expression in SPARC-null cells after 3 days of serum starvation is only about 44% of the wild type cells (FIG. 4), suggesting that decreased expression of cell cycle regulated genes and DNA synthesis in SPARC-null cells results from downregulation of the IGF-1 receptor. Thus, SPARC plays a role in IGF-1 receptor expression and thus insulin/IGF-1 signal transduction.

EXAMPLE 4

Wound Healing

To investigate the role of SPARC in wound healing, full-thickness, cutaneous defects were made on the dorsum of transgenic SPARC deficient mice according to Example 1 and wildtype mice, as follows.

Two- to three-month-old male mice were anesthetized intraperitoneally with avertin (0.5 g/kg body weight). The hair on the back was cut and full-thickness wounds of various sizes were made by excising the skin and panniculus carnosus. The 6-mm diameter wounds provided stable wound beds appropriate for histological and RNA analysis, while the larger wounds were analyzed for temporal variation in wound repair. Wounds were neither dressed nor sutured. Mice were caged individually until they were killed by $CO_2$ asphyxia. The 6-mm diameter wound areas were collected from three mice on various days post-wounding for histological and RNA analysis. An area of 7 to 8 mm in diameter, which included the complete epithelial margins, was removed, bisected in the midtransversal plane, fixed in Buffered Formalde-Fresh (Fisher), and embedded in paraffin. Sections (6 µm) were stained with hematoxylin and eosin. For RNA analysis, biopsies were frozen in liquid nitrogen.

Figure 5A:
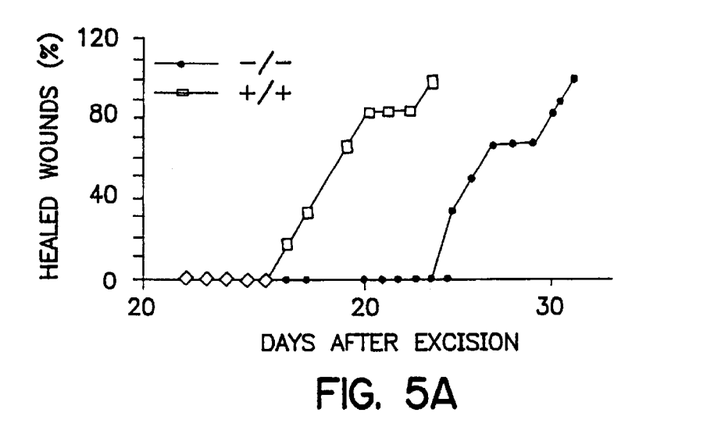
FIG. 5A provides cutaneous wound healing in SPARC-null (−/−) and wild-type (+/+) mice with 25-mm oblong excision wounds. The percentage fractions of SPARC (−/−) and SPARC (+/+) mice (6 in each group) with healing, defined as loss of the wound scab and complete covering of the wound with epidermis, are plotted versus days after the excision.

Examination of full-thickness excision wounds, including panniculus carnosus, on the dorsal skin of wild-type and SPARC-null transgenic mice of the invention indicated that the absence of SPARC impedes healing of skin wounds. In two independent experiments with 25-mm oblong wounds (6 mice of each type), SPARC-null transgenic mice showed delayed progression of healing (FIG. 5A). One day after surgery, both the wild-type and SPARC-null wounds were covered with a clear thin exudate. Build-up of dehydrated wound crusts or scabs began at day 3 and became subsequently more extensive. Scabs in the SPARC-null wounds were thicker with more gaping red wound fields than those in control wounds. In control wild-type mice, loss of wound scabs began at day 17 and was complete in all mice by day 24, with wounds well-healed and epithelial covering restored (FIG. 5A). In contrast, healing of SPARC-null wounds remained incomplete on day 24, with scabs revealing a gaping red wound field. Complete healing in all mice was observed between 25 and 31 days (FIG. 5A). Results with 30-mm circular excision wounds (not shown) were consistent with those described above.

Figure 5B:
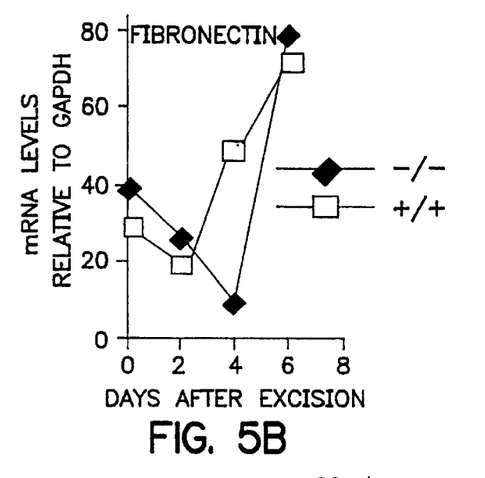
FIG. 5B provides expression of fibronectin in wounds of SPARC-null and wild-type mice (3 in each group).
Figure 5C:
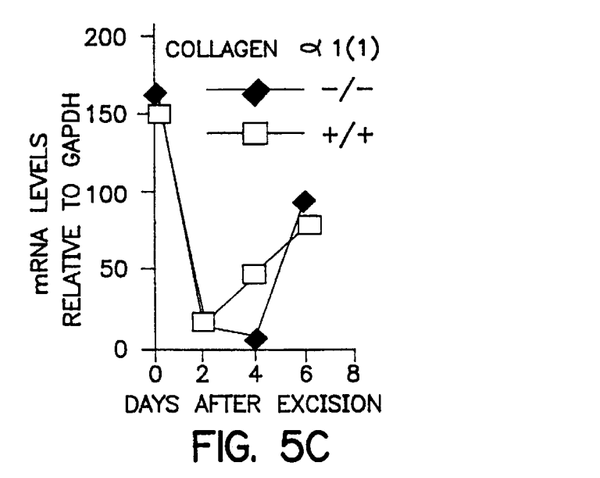
FIG. 5C provides expression of alpha(I) collagen in wounds of SPARC-null and wild-type mice (3 in each group).
Figure 5D:
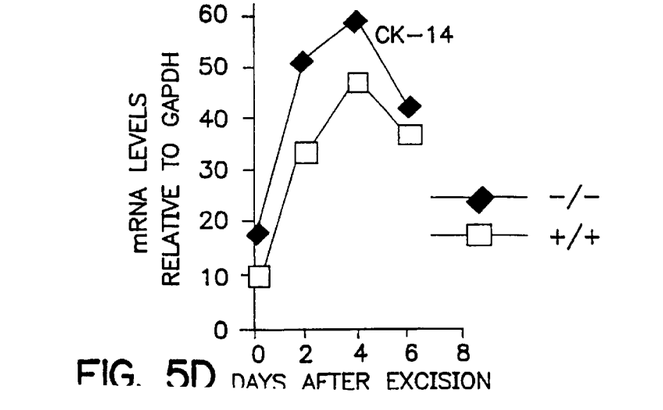
FIG. 5D provides expression of cytokeratin 14 (ck-14) in wounds of SPARC-null and wild-type mice (3 in each group).
Figure 6:
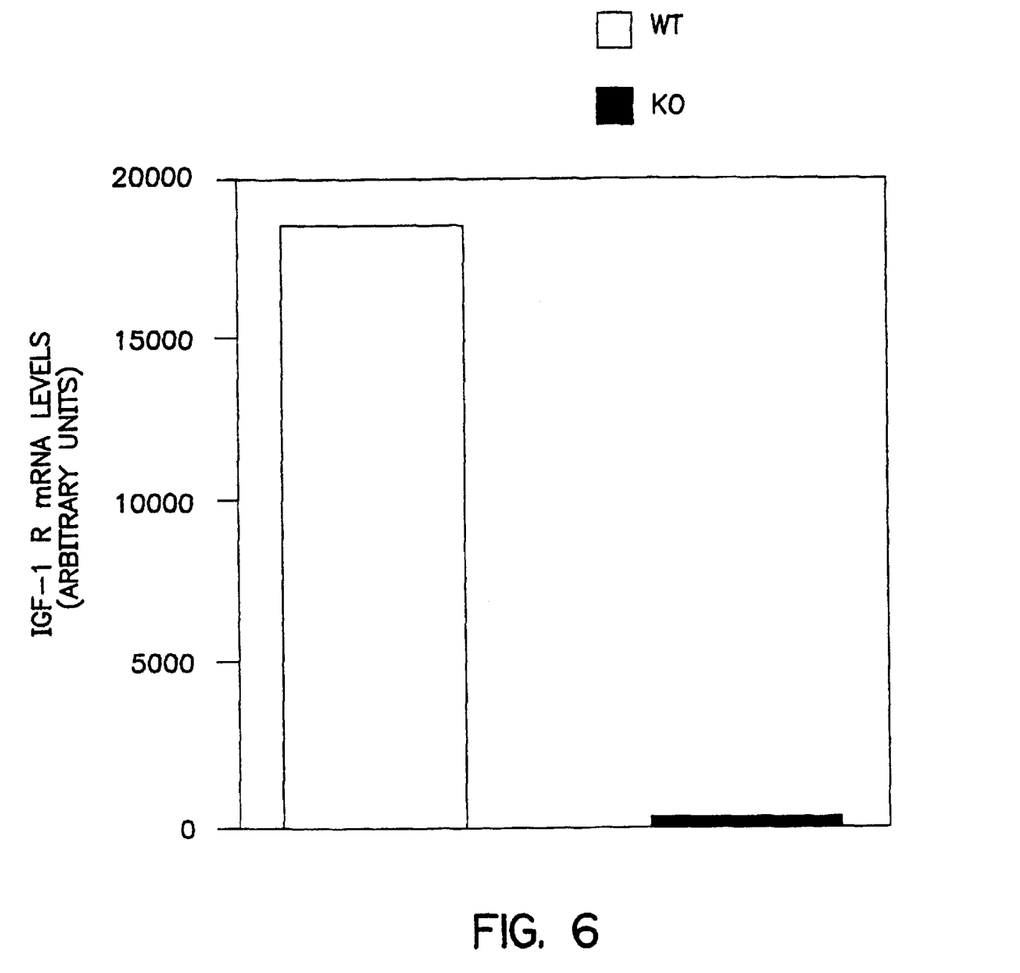
FIG. 6 provides a graph of expression of IGF-1 receptor—mRNA in the 4-day wounds of SPARC-null (−/−) and wild-type (+/+) mice.

The delayed wound closure in SPARC-null transgenic mice may signify impaired cell proliferation. It was found that cytokeratin 14 expression, which is associated with proliferative epidermal keratinocytes at wound sites [Watanabe et. al., Histochem. Cell Biol. 103:425–433 (1995)], commenced immediately after wounding in SPARC-null wounds as in wild-type wounds, with peak expression at day 4 during a 6-day healing period (FIGS. 5B–5D). Histology also indicates normal reepithelialization at the wound sites of the transgenic mice (not shown). However, granulation appeared to be delayed in SPARC-null mice. Northern analysis of Alpha 1(I) collagen and fibronectin expression, which is upregulated in dermal granulation tissue [Gailit and Clark, *Curr. Opin. Cell Biol.*, 6:717–725 (1994); French-Constant et al., *J. Cell Biol.*, 109:903–914 (1989); Scharffetter et. al., *Soc. Invest. Dermatol.*, 93:405–412 (1989)], revealed synthesis of both transcripts in the wounds (6 mm in diameter) of wild-type mice beginning on days 2 to 4, whereas those in SPARC-null transgenic mice did not occur until days 4 to 6 (FIGS. 5B–5D). Consistent with the above immunohistochemical analysis of 25-mm oblong wounds indicated lower fibronectin expression at day 5 in SPARC-null transgenic mice compared to wild-type mice. Histological examination of 6-mm wound sections showed no visible granulation in a 2-day wound of SPARC-null transgenic mice or wild type mice, more extensive granulation at day 4 in the wild-type than in the SPARC-null wounds, and elaborate granulation at 6 days in both types of wounds (not shown). Thus, SPARC deficiency compromises the granulation process which involves fibroblast ingrowth and ECM protein deposition.

This delayed granulation is likely due to decreased IGF-1 receptor expression as revealed by the Northern analysis with TGF-1 receptor precursor [Ullrich et. al., *EMBO J.*, 5:2503–2512 (1986)]. In 4-day wounds of SPARC-null transgenic mice the IGF-1 receptor mRNA was expressed but at a lower level than in wild-type mice. On the other hand, expression was not detected in the wounds of SPARC-null or wild-type mice at day 0, 2 or 6. It would appear that the level of IGF-1 receptor, if expressed, is below the detectable level by Northern analysis when cell division is not occurring (as at day 0) or is complete (as at day 6). The 2-day wounds have very little granulation and thus are not expected to express the receptors. Restoration of the DNA synthesis of SPARC-null fibroblasts treated with insulin by addition of PDGF-AB suggests the importance of compensating growth factors in reinstating the full wound repair process and in the apparently normal development of these mutant mice.

EXAMPLE 5

Cataract Formation

Down-regulation of IGF-1 receptors in SPARC null cells suggests impaired glucose uptake by the cells, a process predisposing the mice to cataract formation. Pupils were first dilated and then mice anesthetized intraperitoneally with avertin (0.5 g/kg body weight). Examination of two 3-month old SPARC-null mice by slit lamp microscope showed that one of them begun to develop cataract in the right eye. However, six 10–12 month-old SPARC-null mice examined all had extensive cataracts. Some of these cataracts were so mature that they showed lens-associated uveitis with lens proteins protruding into the anterior chamber of the eyes. No cataract was found in age-matched (3 month- or 10–12 month-old) wild-type mice.

EXAMPLE 6

Diabetes

Blood glucose levels of ad libitum-fed mice were measured by applying whole blood from the tail veins to the test strips and analyzed with Encore glucometer (Bayer Diagnostic). The blood glucose levels of 3 month-old SPARC-null mice were normal. However the six 10 to 12 month-old SPARC-null mice showing cataracts were statistically higher in the SPARC-null mice than the age matched wild type control mice: wild-type, 124±12 (mean±standard deviation, SD); SPARC(−/−), 151±12 (mean±SD); p:0.005. The results suggest that the transgenic mice may be prone toward hyperglycemia. Fasting blood glucose level measurements, glucose tolerance tests and insulin tolerance tests will be performed to define the observed difference more precisely.

EXAMPLE 7

Proteinuria

As diabetes also affects renal function, urine glucose levels were examined by urine test strips (Chemstrip 2GP, Sigma). No urine glucose was found in transgenic mice at the ages of 3 months, 10 to 12 months, or in age-matched controls. However, the 10 to 12 month old transgenic mice afflicted with cataracts suffer from proteinuria that heralds the onset of renal failure. The test strips from wild type mice turned black about 30 min after application of the urine while those from transgenic mice remained unchanged. The results suggest that the glomerular filters in the SPARC-null kidneys failed to retain some glucose oxidase inhibitors, which found its way into the urine and inhibited the glucose oxidase reaction, hence no change in the color of test strips.

All documents cited above are incorporated by reference herein. Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A transgenic mouse having a genome comprising a disruption in a SPARC gene that prevents expression of functional SPARC protein, wherein said mouse has a phenotype selected from the group consisting of a decreased ability to heal wounds, the development of senile cataracts, the development of hyperglycemia, the development of proteinuria, and the development of osteopenia.

2. The transgenic mouse of claim 1, wherein said disruption is homozygous, and the recombinant introduction of said disruption occurred in said mouse, or an ancestor of said mouse, at an embryonic stage.

3. The transgenic mouse according to claim 1, wherein the disruption is conferred by a transgene integrated into the genome of somatic and germ cells of said mouse which disrupts the endogenous SPARC gene.

4. The transgenic mouse according to claim 1, wherein the mouse is fertile.

5. The transgenic mouse according to claim 1 wherein the transgene is a DNA molecule consisting of a 9.3 kb fragment containing exons 2 to 5 of the SPARC gene and a neo resistance gene, wherein said neo resistance gene is inserted within said 9.3 kb fragment.

6. A cell isolated from the transgenic mouse of claim 1, wherein said cell does not express functional SPARC.

7. The cell according to claim 6 containing pSPARC2-5neo/TK, ATCC number 97335.

8. A stable cell line established from a cell isolated from said transgenic mouse of claim 1, wherein said cell line does not express functional SPARC.

9. A method for producing a transgenic mouse comprising introducing into a mouse embryonic stem cell, wherein the embryonic stem cell expresses functional SPARC, a transgene comprising a disrupted SPARC DNA sequence such that the introduction results in the disruption of the genomic SPARC gene sequence of said embryonic stem cell, and wherein the development of a mouse from said SPARC-disrupted embryonic stem cell produces a transgenic mouse lacking functional SPARC, and wherein said mouse has a phenotype selected from the group consisting of a decreased ability to heal wounds, the development of senile cataracts, the development of hyperglycemia, the development of proteinuria, and the development of osteopenia.

10. The method according to claim 9, further comprising the steps of:
   injecting said cell into an embryo of said mouse;
   transplanting said embryo into a pseudopregnant mouse;
   allowing said embryo to develop to term,
   identifying at least one transgenic offspring containing said transgene, and
   breeding said offspring to form a transgenic mouse, wherein said mouse cannot express SPARC.

11. The method according to claim 9, wherein the transgene integrates into the genome of said cell.

12. The method according to claim 9, wherein said transgene is a DNA molecule consisting of a 9.3 kb fragment containing exons 2 to 5 of the SPARC gene and a neo resistance gene, wherein said neo resistance gene is inserted within said 9.3 kb fragment.

13. A method of screening a compound for an effect on the SPARC null phenotype, comprising the steps of:
   (a) administering a test compound to the transgenic mouse of claim 1;
   (b) administering said compound to a control mouse that expresses functional SPARC; and
   (c) observing whether said compound produces an effect on a phenotype selected from the group consisting of the ability to heal wounds, the development of senile cataracts, the development of hyperglycemia, the development of proteinuria, and the development of osteopenia in said transgenic mouse as compared to the control mouse.

14. The method according to claim 13, wherein said compound is a polynucleotide molecule comprising a polynucleotide sequence encoding SPARC under the control of regulatory sequences which permit expression of SPARC.

15. The method according to claim 14 wherein said polynucleotide molecule is a DNA molecule.

16. The method according to claim 14 wherein said polynucleotide molecule is selected from the group consisting of viral vectors and plasmid vectors.

17. The method according to claim 13, wherein said compound is a polynucleotide.

18. The method according to claim 17, wherein said polynucleotide is a DNA molecule.

19. The method according to claim 17, wherein said polynucleotide is selected from the group consisting of viral vectors and plasmid vectors.

20. A method of screening a compound for an effect on SPARC-expressing and SPARC-non-expressing cells, comprising the steps of:
   (a) introducing a test compound to a population of cells, or a homogenate thereof, wherein said cells are isolated or established from the transgenic mouse of claim 1, wherein the cells do not express functional SPARC;
   (b) administering said compound to a control mouse cell population, or homogenate thereof, that expresses functional SPARC; and
   (c) observing or assaying whether said compound produces an effect on SPARC-expression in the cells of said transgenic mouse as compared to control mouse cells.

21. The method according to claim 20, wherein said compound is polynucleotide encoding SPARC.

22. The method according to claim 21, wherein said polynucleotide is a DNA molecule and is operatively linked to a promoter.

23. The method according to claim 21 wherein said polynucleotide molecule is selected from the group consisting of viral vectors and plasmid vectors.

24. The method according to claim 20, wherein said compound is a polynucleotide molecule comprising an antisense SPARC polynucleotide sequence.

25. The method according to claim 20, wherein said compound is a polynucleotide.

26. The method according to claim 25, wherein said polynucleotide is a DNA molecule.

27. The method according to claim 25, wherein said compound is polynucleotide selected from the group consisting of viral vectors and plasmid vectors.

* * * * *